United States Patent
Oshima

(10) Patent No.: US 11,173,143 B2
(45) Date of Patent: Nov. 16, 2021

(54) COMPOSITION FOR DECREASING SERUM URIC ACID LEVEL

(71) Applicant: ASAHI GROUP HOLDINGS, LTD., Tokyo (JP)

(72) Inventor: Shunji Oshima, Moriya (JP)

(73) Assignee: ASAHI GROUP HOLDINGS, LTD., Tokyo (JP)

( * ) Notice: Subject to any disclaimer, the term of this patent is extended or adjusted under 35 U.S.C. 154(b) by 0 days.

(21) Appl. No.: 16/642,687

(22) PCT Filed: Aug. 1, 2018

(86) PCT No.: PCT/JP2018/028932
§ 371 (c)(1),
(2) Date: Feb. 27, 2020

(87) PCT Pub. No.: WO2019/044348
PCT Pub. Date: Mar. 7, 2019

(65) Prior Publication Data
US 2020/0253928 A1 Aug. 13, 2020

(30) Foreign Application Priority Data
Aug. 30, 2017 (JP) .............................. JP2017-165645

(51) Int. Cl.
*A61K 31/405* (2006.01)
*A61P 19/06* (2006.01)
*A61K 31/198* (2006.01)

(52) U.S. Cl.
CPC .......... *A61K 31/405* (2013.01); *A61K 31/198* (2013.01); *A61P 19/06* (2018.01)

(58) Field of Classification Search
CPC .................................................... A61K 31/405
USPC ......................................................... 514/419
See application file for complete search history.

(56) References Cited

FOREIGN PATENT DOCUMENTS

| EP | 1 374 863 A1 | 1/2004 | |
|---|---|---|---|
| JP | 2002-275059 A | 9/2002 | |
| JP | 2003-116504 A | 4/2003 | |
| JP | 2011-098896 A | 5/2011 | |
| JP | 2016-050198 A | 4/2016 | |
| WO | WO 02.074303 | * 9/2002 | ........... A61K 31/198 |
| WO | 2016/158212 A1 | 10/2016 | |

OTHER PUBLICATIONS

Oshima, Nutrients 2019, 11, 564, 1-11.*
Yu TF, et al., "Effect of Glycine Loading on Plasma and Urinary Uric Acid and Amino Acids in Normal and Gouty Subjects", The American Journal of Medicine, 1970, pp. 352-359, vol. 49.
International Search Report for PCT/JP2018/028932 dated Oct. 23, 2018 [PCT/ISA/210].
International Preliminary Report on Patentability with Written Opinion of the International Searching Authority for PCT/JP2018/028932 dated Mar. 12, 2020.

* cited by examiner

*Primary Examiner* — Nizal S Chandrakumar
(74) *Attorney, Agent, or Firm* — Sughrue Mion, PLLC

(57) ABSTRACT

Provided is a composition for reducing serum uric acid level, which contains glycine and tryptophan. The serum uric acid level in a subject can be decreased when the subject intakes the composition.

9 Claims, 1 Drawing Sheet

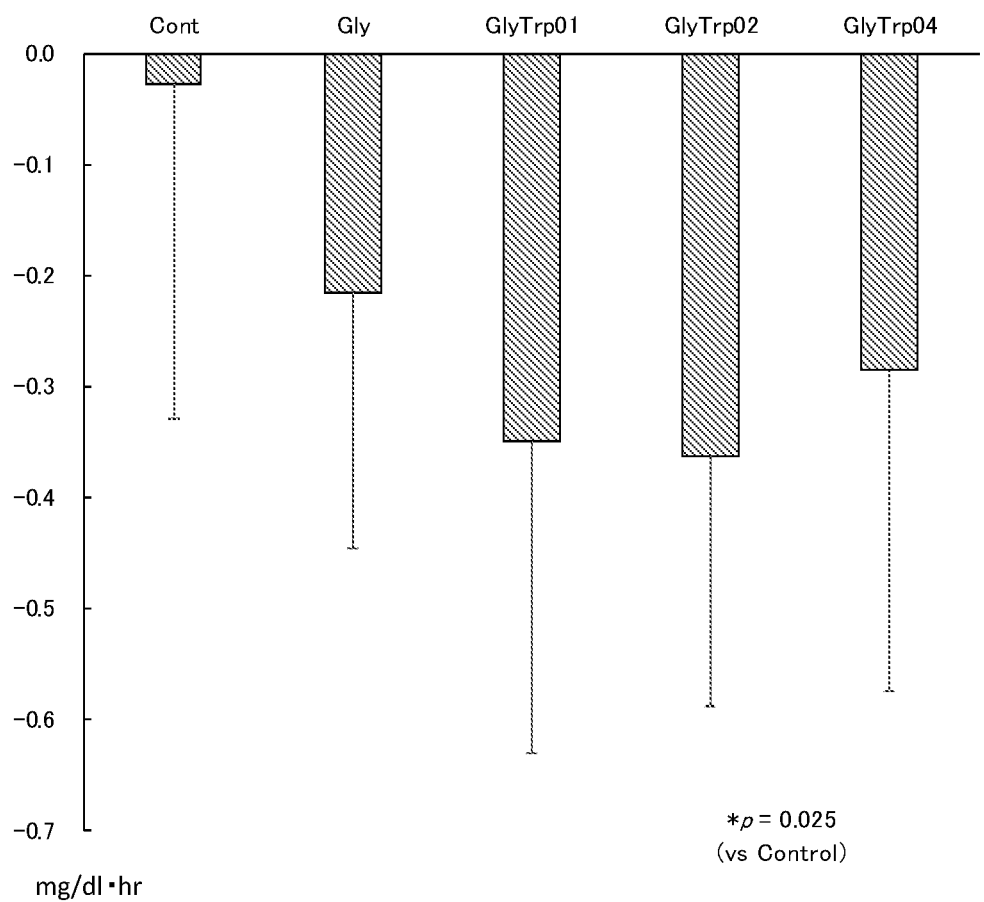

COMPOSITION FOR DECREASING SERUM URIC ACID LEVEL

CROSS REFERENCE TO RELATED APPLICATIONS

This application is a National Stage of International Application No. PCT/JP2018/028932 filed Aug. 1, 2018, claiming priority based on Japanese Patent Application No. 2017-165645 filed Aug. 30, 2017 and which Japanese Patent Application No. 2017-165645 is incorporated herein by reference in its entirety.

BACKGROUND OF THE INVENTION

Technical Field

The present invention relates to a composition for reducing serum uric acid level.

Description of the Related Art

Uric acid is a final metabolite of purines, and the uric acid produced is excreted in urine. Normally, the amounts of uric acid produced and excreted are balanced. When the uric acid level in serum is 7 mg/dl or greater for some reason, it is called hyperuricemia. When hyperuricemia becomes chronic, the risk of, for example, gout increases. As therapeutic agents for hyperuricemia, uric acid production inhibitors and uric acid excretion enhancers are known. However, there is a concern of side effects.

Glycine, which is the simplest amino acid, is known to have an effect of increasing uric acid excretion. However, excessive intake of glycine is considered to have a possibility of increasing uric acid level through nucleic acid synthesis. Glycine is also known to have an effect of increasing in vivo alcohol disappearance rate (refer to, for example, Japanese Patent Application Publication No. 2003-116504). In addition, a composition that contains orotic acid and a specific amino acid as active ingredients is known to have a uric acid level-lowering effect (refer to, for example, Japanese Patent Application Publication No. 2011-98896).

BRIEF SUMMARY

Problems to be Solved by the Invention

The present invention is directed to providing a composition capable of reducing serum uric acid level.

Means for Solving the Problem

An aspect of the present invention provides a composition containing glycine and tryptophan for reducing serum uric acid level.

In a certain aspect, the composition has a ratio of tryptophan to glycine in the range of 0.01 and 0.15.

In a certain aspect, glycine intake per dose of the composition is in the range of 1 g and 10 g.

In addition, an aspect of the present invention provides a food and drink product containing the composition.

In addition, an aspect of the present invention provides a serum uric acid level reducer containing the composition.

An aspect of the present invention provides a composition that contains glycine and tryptophan and reduces serum uric acid level, a method for reducing serum uric acid level including administering the composition that contains glycine and tryptophan to a subject, and a use of the composition that contains glycine and tryptophan in producing a serum uric acid level reducer.

Effect of the Invention

According to the present invention, a composition capable of reducing serum uric acid level can be provided.

BRIEF DESCRIPTION OF DRAWINGS

FIG. 1 is a graph showing decreases in uric acid concentrations in serum in three hours from the start of a test.

DETAILED DESCRIPTION

In the present specification, for the amount of each component contained in a composition, when a plurality of substances corresponding to the component exist, the amount of the component means the total amount of the substances present in the composition unless otherwise specified.

Composition for Reducing Serum Uric Acid Level

The composition for reducing serum uric acid level contains glycine and tryptophan as active ingredients, and may further contain other ingredients as necessary. Although glycine is known to have an effect of reducing serum uric acid level, the effect of reducing serum uric acid level improves synergistically when used in combination with glycine.

For example, alcohol intake is known to usually increase serum uric acid level temporarily. The main causes are seemingly that uric acid is produced when alcohol is broken down in the body, and that lactic acid produced from alcohol metabolism causes uric acid to accumulate in the body. Administering the composition containing glycine and tryptophan can effectively suppress such an increase in uric acid level.

In this specification, reducing serum uric acid level includes lowering a uric acid level higher than normal serum uric acid level (for example, less than 7 mg/dl) and lowering a serum uric acid level increased by some factor (for example, alcohol intake). Such a decrease in serum uric acid level can be demonstrated by measuring the serum uric acid levels and comparing them with those of the control group.

Glycine, or aminoacetic acid, is an amino acid having the simplest structure. The purity of glycine is not particularly limited as long as it is appropriate for administration to the human body. For example, the purity is 90% or more, and preferably 98% or more. The glycine can be produced by, for example, an extraction method or a microbial fermentation method, or may be appropriately selected from commercially available products.

Tryptophan refers to 2-amino-3-indolyl propionic acid, and is only required to contain at least L-tryptophan. The tryptophan may be a racemate, but is preferably L-tryptophan. The purity of tryptophan is not particularly limited as long as it is appropriate for administration to the human body. For example, the purity is 90% or more, and preferably 98% or more. The tryptophan can be produced by, for example, an extraction method or a microbial fermentation method, or may be appropriately selected from commercially available products.

The glycine and tryptophan may be contained each in the form of a simple substance (free form) or in the form of a salt. The salts of glycine and tryptophan are not particularly limited as long as they are pharmacologically acceptable salts. Specific examples include acid addition salts, metal salts, ammonium salts, and organic amine addition salts. Examples of the acid addition salts include inorganic acid salts, such as hydrochloride, sulfate, nitrate, and phosphate; and organic acid salts, such as acetate, maleate, fumarate, citrate, malate, lactate, α-ketoglutarate, gluconate, and caprylate. Examples of the metal salts include alkali metal salts, such as sodium salt and potassium salt; alkaline earth metal salts, such as magnesium salt and calcium salt; aluminum salt, and zinc salt. Examples of the ammonium salts include salts of ammonium and tetramethylammonium. Examples of the organic amine addition salts include salts of morpholine and piperidine.

The weight ratio of tryptophan to glycine in the composition ranges of, for example, 0.01 and 0.15, preferably 0.012 and 0.1, more preferably 0.015 and 0.09, still more preferably 0.015 and 0.08, and even more preferably 0.015 and 0.07 to achieve serum uric acid level reducing effect. Also, the weight ratio of tryptophan to glycine in the composition is, for example, 0.01 or more, 0.012 or more, 0.015 or more, 0.02 or more, 0.03 or more, 0.04 or more, 0.05 or more, or 0.06 or more, and also, for example, 0.15 or less, 0.1 or less, 0.09 or less, 0.08 or less, or 0.07 or less.

The composition may further contain other active ingredients in addition to glycine and tryptophan. Such other active ingredients are only required to have a serum uric acid level reducing effect. Examples of such other active ingredients include other amino acids, such as alanine, arginine, asparagine, aspartic acid, cysteine, glutamine, glutamic acid, glycine, histidine, isoleucine, leucine, lysine, methionine, phenylalanine, proline, serine, threonine, tyrosine, and valine. Among such other amino acids, aspartic acid, asparagine, glutamic acid, or glutamine is preferable, asparagine, glutamic acid, or glutamine is more preferable, and asparagine or glutamic acid is still more preferable. Such other amino acids may be used alone or as a combination of two or more.

Examples of such other active ingredients can further include known serum uric acid level-reducing agents including uric acid production inhibitors, such as allopurinol and febuxostat, and uric acid excretion promoting agents, such as benzbromarone and probenecid. These may be used alone or as a combination of two or more.

The total active ingredient content of the composition can be suitably selected in accordance with, for example, the structure of the composition and the desired administration effect of the composition. The total active ingredient content of the composition is, for example, 0.0001% by weight or more, preferably 0.001% by weight or more, more preferably 0.01% by weight or more, and also, for example, 100% by weight or less, preferably 70% by weight or less, and more preferably 50% by weight or less.

The composition may further contain other ingredients in addition to the active ingredients as necessary. Examples of such other ingredients include solvents such as water; various vitamins including B vitamins, sweeteners, fragrances, coloring agents, pharmacologically acceptable carriers, excipients, diluents, salts, pH adjusters, chelating agents, and buffering agents.

The composition may take any dosage form, such as powder, granule, tablet, capsule, troche, syrup, liquid, and injection. The administration method is selected from typical administration routes in accordance with, for example, the dosage form of the composition. Examples of the administration routes include oral administration, nasal administration, rectal administration, intravenous injection, and drip infusion.

The dosage of the composition is an amount that enables its serum uric acid level reducing effect to be achieved. The dosage per dose of glycine is usually 1 g or more, preferably 1.5 g or more, preferably 2 g or more, 3 g or more, 4 g or more, or 5 g or more, and also, for example, 10 g or less, preferably 8 g or less, 7 g or less, or 6 g or less. The dosage per dose of tryptophan is usually 0.01 g or more, preferably 0.05 g or more, 0.1 g or more, or 0.15 g or more, and, for example 1.0 g or less, preferably 0.6 g or less. 0.5 g or less, 0.4 g or less, or 0.35 g or less. The frequency of daily administration is, for example, from 1 to 3 times.

Pharmaceutical Composition

The composition can be used as a pharmaceutical composition for preventing and/or treating a disease whose pathological condition is improved by reducing serum uric acid level. Examples of such diseases include gout, hyperuricemia, gouty tophus, urinary calculi (renal stones, ureteral stones, bladder stones), renal failure, gout kidneys, prostatic hypertrophy, and edema. The composition can also serve as a prophylactic agent that curbs the onset of the above diseases and/or a therapeutic agent that ameliorates such diseases to recover a normal state.

When the composition is used as a medicament for preventing and/or treating a disease, it can be safely administered orally or parenterally to mammals such as humans, mice, rats, rabbits, dogs, and cats. The dosage of the composition can be appropriately determined in accordance with the type of disease, the age, sex, body weight, symptom severity of the subject, or the administration method. For example, when orally administered to, for example, gout patients or hyperuricemia patients, the composition is administered once to several times a day such that the total of glycine and tryptophan is usually 1 g or more, preferably 1.5 g or more, 2 g or more, 3 g or more, 4 g or more, or 5 g or more, or, for example, 10 g or less, preferably 8 g or less, 7 g or less, 6 g or less, 5 g or less, or 4 g or less. The administration period is, for example, 1 day or more and 1 year or less, and preferably 1 week or more and 3 months or less.

Food and Drink Product

The food and drink product contains the above-described glycine and tryptophan-containing composition for reducing serum uric acid level. The effect of the composition described above can be acquired by ingesting the food and drink product. Examples of the food and drink product containing the composition for reducing serum uric acid level include all food and drink products into which the composition for reducing serum uric acid level can be mixed, in addition to, for example, healthy food and drink products, functional food and drink products, and food and drink products for the sick. Among these, functional food and drink products are particularly preferable. "Functional food and drink products" means food and drink products having certain functionality with respect to the living body, and the examples include health food and drink products in general including food and drink products with health claims, for example, food and drink products for specified health use (including conditional tokuho or food products for specified health use) and health function food and drink products with nutrient function claims, special-purpose food and drink products, nutrition-supplementing food and drink products, health supplementing food and drink products, supplements (in various forms, such as tablets, coated tablets, dragees, capsules, and liquids) and beauty food and drink products (for example, diet food and drink products). Functional food and drink products also include health food and drink products to which health claims based on the food standards of Codex (FAO/WHO Joint Food Standards Committee) are applied.

These health food products may be in the form of normal food products, or in the form of supplements such as pills, granules (for example, granules packed in sticks), fine granules, tablets, chewable tablets, and capsules (for example, soft or hard capsules).

The food and drink product may be beverages with fluidity. When the food and drink product is a beverage with fluidity, the glycine concentration in the beverage is, for example, 0.1 g/100 ml or more, preferably 0.3 g/100 ml or more, and more preferably 0.6 g/100 ml or more, and also, for example, 10 g/100 ml or less, preferably 8 g/100 ml or less, and more preferably 7 g/100 ml or less. The tryptophan concentration in the beverage is, for example, 0.001 g/100 ml or more, preferably 0.005 g/100 ml or more, and more preferably 0.02 g/100 ml or more, and also, for example 1.0 g/100 ml or less, preferably 0.6 g/100 ml or less, and more preferably 0.4 g/100 ml or less.

The beverage includes, for example, the composition containing glycine and tryptophan and a liquid medium such as water or fruit juice. Examples of the beverage include tea beverages such as green tea, oolong tea and black tea, refreshing drinks, jelly drinks, sports drinks, milk drinks, carbonated drinks, vegetable drinks, fruit juice drinks, fermented vegetable drinks, fermented fruit juice drinks, fermented milk drinks (for example, yogurt), lactic acid bacteria beverages, milk beverages (for example, coffee milk, fruit milk), powdered beverages, cocoa beverages, and alcoholic beverages. The beverage may be a beverage containing the composition and using milk and purified water as liquid media.

The beverage may contain a sweetener to adjust sweetness. The sweetener may be a sugar, and examples of the sugar include sucrose, glucose, fructose, fructooligosaccharide, and galactooligosaccharide. Alternatively, synthetic sweeteners such as aspartame and saccharin may be added instead of sugar.

The beverage may contain an acidulant. Examples of the acidulant include citric acid, DL-malic acid, L-tartaric acid, lactic acid, and phosphoric acid.

The beverage may contain a fragrance. Examples of the fragrance include citrus oil such as lemon, lime, and orange; orange oil; and herb extract. The fragrance may be a natural fragrance or a synthetic fragrance. Examples of the natural fragrance include anise oil, angelica oil, allspice oil, orange oil, cassia oil, capsicum oil, guarana extract, cardamom oil, caraway oil, cumin oil, clarisage oil, grapefruit oil, clove oil, coriander oil, coffee oil, cognac oil, cola nut extract, cinnamon oil, ginger oil, thyme oil, nutmeg oil, mentha oil, vanilla extract, bitter almond oil, fenugreek oil, fennel oil, pepper oil, peppermint oil, perilla oil, bergamot oil, mandarin oil, eucalyptus oil, lemon oil, and rosemary oil.

Examples of the synthetic fragrance include anethole, allyl caproate, isoamyl acetate, γ-undecalactone, ethyl vanillin, ethyl butyrate, ethyl phenyl glycidate, eugenol, geraniol, diacetyl, cycloten, citral, cinnamic aldehyde, terpineol, δ-decalactone, decanal, nonanal, γ-nonalactone, vanillin, phenylethyl alcohol, furaneol, furfuryl mercaptan, 2-hexenal, 3-hexenol, heliotropin, perillaaldehyde, benzaldehyde, maltol, methylanthranilate, methyl salicylate, menthol, α-ionone, and linalool.

EXAMPLES

The present invention will now be described by means of examples; however, the present invention is not limited to these examples.

Example 1

Tests were conducted with healthy adult men and women as subjects after their written informed consents were obtained. The subjects were orally administered with any of 6 g of poorly soluble dextrin (n=7; Cont) as a control, 6 g of glycine (n=7; Gly), a composition containing 6 g of glycine and 0.1 g of tryptophan (n=5; GlyTrp01), a composition containing 6 g of glycine and tryptophan 0.2 g (n=7; GlyTrp02), and a composition containing 6 g of glycine and 0.4 g of tryptophan (n=7; GlyTrp04). Thirty minutes later, a korui shochu was given to the subjects at 0.32 g/kg amount of alcohol. Their blood samples were collected before the intake of the composition, 60 minutes, 120 minutes, and 180 minutes after the intake to measure the serum uric acid concentrations (mg/dl). Table 1 shows the measurement results. Table 1 also shows probabilities (p value) in the t test for the significant difference between the values measured before the intake of the composition (0) and at each elapsed time as changes in serum uric acid concentrations over time.

TABLE 1

| | Uric acid concentrations in serum | | | | Change over time (p value) | | |
|---|---|---|---|---|---|---|---|
| | 0 | After 60 min | After 120 min | After 180 min | After 60 min | After 120 min | After 180 min |
| Cont | 5.2 | 5.2 | 5.1 | 5.2 | 0.802 | 0.504 | 1.000 |
| Gly | 5.2 | 5.1 | 5.0 | 5.0 | 0.250 | 0.051 | 0.026 |
| GlyTrp01 | 5.8 | 5.7 | 5.7 | 5.6 | 0.109 | 0.160 | 0.033 |
| GlyTrp02 | 5.1 | 4.9 | 4.9 | 4.9 | 0.000 | 0.020 | 0.024 |
| GlyTrp04 | 5.8 | 5.7 | 5.6 | 5.6 | 0.308 | 0.495 | 0.339 |

Table 1 shows no change over time in the serum uric acid concentrations of the control group (Cont), but shows a tendency of decrease over time in the serum uric acid concentrations of the groups administered with a composition containing glycine and tryptophan. In particular, the group administered with a composition containing 6 g of glycine and 0.2 g of tryptophan (GlyTrp02) showed a significant decrease in serum uric acid concentrations for 180 minutes from the start of the measurement.

Based on the measured values of serum uric acid concentrations, the area under the serum uric acid concentration-time curve ($AUC_{0 \to 3\ h}$) from before the intake (0) to 180 minutes after the intake of the composition was calculated. The uric acid concentration-time curve is a curve showing a decrease in the uric acid concentration over time using the uric acid concentration before taking the composition as a reference (0). The results are shown in FIG. 1.

FIG. 1 shows that AUC tends to decrease in the groups administered with the compositions containing glycine and tryptophan, and in particular, AUC falls significantly (p=0.025) in the group administered with the composition containing 6 g of glycine and 0.2 g of tryptophan (GlyTrp02) with respect to the control group (Cont).

Example 2

Tests were conducted with subjects with hyperuricemia having high serum uric acid levels (7.1 mg/dl or higher) after their written informed consents were obtained. The control group took 3 g of glycine (n=4) and the composition intake group took a composition containing 3 g of glycine and 0.2 g of tryptophan (n=4) daily for 8 weeks. Their serum uric acid levels were measured before the intake and after 8 weeks of the intake. The results are shown in Table 2. A sign test was used as the test of significance.

TABLE 2

| Subject | Before start of intake | After 8 weeks | Amount of change |
|---|---|---|---|
| <Control group> | | | |
| A | 8.9 | 9.3 | 0.4 |
| B | 7.8 | 7.8 | 0.0 |
| C | 7.1 | 6.6 | −0.5 |
| D | 7.1 | 6.7 | −0.4 |
| Average | 7.73 | 7.60 | −0.13 |
| Standard deviation | 0.74 | 1.09 | 0.36 |
| Significant difference | — | 0.257 | — |
| <Composition intake group> | | | |
| E | 7.6 | 7.4 | −0.2 |
| F | 7.4 | 6.4 | −1.0 |
| G | 7.2 | 6.9 | −0.3 |
| H | 7.1 | 6.8 | −0.3 |
| Average | 7.33 | 6.88 | −0.45 |
| Standard deviation | 0.19 | 0.36 | 0.32 |
| Significant difference | — | 0.046 | — |

In the control group who took 3 g of glycine alone, serum uric acid levels were slightly decreased after 8 weeks of continuous intake, but the decreases were not significant. In contrast, in the composition intake group who took the composition containing 3 g of glycine and 0.2 g of tryptophan, serum uric acid levels were significantly decreased after 8 weeks of continuous intake.

The disclosure of Japanese Patent Application Publication No. 2017-165645 (filing date: Aug. 30, 2017) is incorporated herein by reference in its entirety. All documents, patent applications, and technical standards mentioned in the present specification are incorporated by reference to the same extent as when each individual document, patent application, and technical standard are specifically and individually stated to be incorporated herein by reference.

The invention claimed is:

1. A method for reducing serum uric acid level, comprising administrating a composition containing glycine and tryptophan,
    wherein the composition has a weight ratio of tryptophan to glycine in the range of 0.01 and 0.15, and
    wherein glycine intake is in the range of 1 g and 10 g per dose.

2. The method according to claim 1, treating a disease whose pathological condition is improved by reducing serum uric acid level,
    wherein the disease is at least one selected from the group consisting of gout, hyperuricemia, gouty tophus, renal failure, gout kidneys, prostatic hypertrophy, edema, and urinary calculi including renal stones, ureteral stones, and bladder stones.

3. The method according to claim 1, wherein the composition further comprises at least one selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tyrosine, and valine.

4. The method according to claim 1, wherein the composition further comprises at least one selected from the group consisting of a uric acid production inhibitor and a uric acid excretion promoting agent.

5. The method according to claim 4, wherein the composition comprises a uric acid production inhibitor.

6. The method according to claim 5, wherein the uric acid production inhibitor is selected from the group consisting of allopurinol and febuxostat.

7. The method according to claim 4, wherein the composition comprises a uric acid excretion promoting agent.

8. The method according to claim 7, wherein the uric acid excretion promoting agent is selected from the group consisting of benzbromarone and probenecid.

9. The method according to claim 1, wherein a total active ingredient content of the composition is 0.0001% by weight or more and 100% by weight or less.

* * * * *